US011298334B2

(12) United States Patent
Cheng et al.

(10) Patent No.: US 11,298,334 B2
(45) Date of Patent: Apr. 12, 2022

(54) USE OF ISOTHIOCYANATE COMPOUNDS (71) Applicant: JC (WUXI) COMPANY, INC., Jiangsu (CN)

(72) Inventors: Jingcai Cheng, Jiangsu (CN); Chunxia Zhang, Jiangsu (CN); Zhiwei Cheng, Jiangsu (CN)

(73) Assignee: JC (WUXI) COMPANY, INC., Jiangsu (CN)

( * ) Notice: Subject to any disclaimer, the term of this patent is extended or adjusted under 35 U.S.C. 154(b) by 385 days.

(21) Appl. No.: 16/097,535

(22) PCT Filed: Apr. 20, 2017

(86) PCT No.: PCT/CN2017/081292
§ 371 (c)(1),
(2) Date: Jan. 4, 2019

(87) PCT Pub. No.: WO2017/181972
PCT Pub. Date: Oct. 26, 2017

(65) Prior Publication Data
US 2019/0142780 A1 May 16, 2019

(30) Foreign Application Priority Data

Apr. 22, 2016 (CN) .......................... 201610257997.8
Apr. 22, 2016 (CN) .......................... 201610258064.0

(51) Int. Cl.
| | | |
|---|---|---|
| *A61K 31/26* | (2006.01) |
| *A61K 31/5375* | (2006.01) |
| *A61K 45/06* | (2006.01) |
| *A61K 31/695* | (2006.01) |
| *A61K 31/277* | (2006.01) |
| *A61K 31/655* | (2006.01) |
| *A61K 45/00* | (2006.01) |
| *A23L 33/10* | (2016.01) |
| *A61P 3/06* | (2006.01) |
| *A61K 31/10* | (2006.01) |
| *A61K 31/132* | (2006.01) |
| *A61K 31/14* | (2006.01) |
| *A61K 31/16* | (2006.01) |
| *A61K 31/202* | (2006.01) |
| *A61K 31/22* | (2006.01) |
| *A61K 31/366* | (2006.01) |
| *A61K 31/40* | (2006.01) |
| *A61K 31/405* | (2006.01) |
| *A61K 31/455* | (2006.01) |
| *A61K 31/505* | (2006.01) |
| *A61K 38/48* | (2006.01) |
| *A61K 49/00* | (2006.01) |

(52) U.S. Cl.
CPC .............. *A61K 31/26* (2013.01); *A23L 33/10* (2016.08); *A61K 31/10* (2013.01); *A61K 31/132* (2013.01); *A61K 31/14* (2013.01); *A61K 31/16* (2013.01); *A61K 31/202* (2013.01); *A61K 31/22* (2013.01); *A61K 31/277* (2013.01); *A61K 31/366* (2013.01); *A61K 31/40* (2013.01); *A61K 31/405* (2013.01); *A61K 31/455* (2013.01); *A61K 31/505* (2013.01); *A61K 31/5375* (2013.01); *A61K 31/655* (2013.01); *A61K 31/695* (2013.01); *A61K 38/486* (2013.01); *A61K 45/00* (2013.01); *A61K 45/06* (2013.01); *A61K 49/0008* (2013.01); *A61P 3/06* (2018.01); *C12Y 304/21011* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 5,589,504 A | * | 12/1996 | Dannenberg | ........... A61K 31/05 514/456 |
| 2014/0271923 A1 | * | 9/2014 | Reid | .................... A61K 31/496 424/651 |

FOREIGN PATENT DOCUMENTS

| | | | | | |
|---|---|---|---|---|---|
| EP | 1216625 A1 | * | 6/2002 | ............. A23L 33/26 |
| JP | 2006-109754 | | 4/2006 | |

OTHER PUBLICATIONS

Navarro et al. Cancer Prevention Research (2009) 2(4): 345-352 (Year: 2009).*
Li et al., "Research progress in chemical constituents of Lepidium apetalum and Descurainia sophia and their pharmacological activities", Drug Evaluation Research, vol. 36, No. 3, Jun. 2013, 6 pages (English abstract enclosed and cited in the ISR).
International Search Report, issued in the corresponding PCT application No. PCT/CN2017/081292, dated Jul. 26, 2017, 8 pages.

* cited by examiner

*Primary Examiner* — Susan M Hanley
(74) *Attorney, Agent, or Firm* — Hamre, Schumann, Mueller & Larson, P.C.

(57) ABSTRACT

Disclosed is the use of isothiocyanate compounds. In particular, disclosed is the use of a compound as shown by Formula (I) or a derivative as shown by Formula (II) in the manufacture of a composition or preparation for preventing and/or treating hyperlipidemia. The compound of the present invention can reduce the levels of triglycerides and low density lipoproteins in the serum of mammals (such as rats and humans), increase the level of high density lipoproteins in the serum, and reduce the level of total bilirubin in the serum of mammals (such as rats and humans).

9 Claims, 3 Drawing Sheets

USE OF ISOTHIOCYANATE COMPOUNDS

TECHNICAL FIELD

The present invention relates to the field of medicine, and in particular, to the use of isothiocyanate compounds.

BACKGROUND ART

Hyperlipidemia refers to abnormal fat metabolism or transportation, which makes the level of one or more lipids in the plasma higher than the normal level. Hyperlipidemia is a systemic disease in which blood cholesterol (TC) and/or triglyceride (TG) is too high or high-density lipoprotein cholesterol (HDL-C) is too low. It is called dyslipidemia in modern medicine. Lipid is insoluble or slightly soluble in water and must be present in the form of lipoprotein after it binds with protein. Therefore, hyperlipidemia is usually hyperlipoproteinemia, in which serum lipoprotein concentration is increased.

The damage to body caused by hyperlipidemia is insidious, gradual, progressive and systemic. Its direct damage is to accelerate systemic atherosclerosis, because the vital organs of the whole body rely on the arteries for blood supply and oxygen supply. Once the artery is blocked by atherosclerotic plaque, it will lead to serious consequences. Kidney failure and the other diseases caused by arteriosclerosis are closely related to hyperlipidemia. A large number of studies have shown that hyperlipidemia is an independent and important risk factor for stroke, coronary heart disease, myocardial infarction, and sudden cardiac death.

In addition, hyperlipidemia is also an important risk factor for promoting hypertension, impaired glucose tolerance, and diabetes. Hyperlipidemia can also lead to fatty liver, cirrhosis, cholelithiasis, pancreatitis, fundus hemorrhage, blindness, peripheral vascular disease, lameness, hyperuricemia. Some patients with primary and familial hyperlipidemia may also have tendinous, nodular, palmar plane and yellow tumor around the eyelid, and arcus juvenilis.

With the improvement of people's living standards, the incidence of hyperlipidemia is increasing. As for persons with excessive blood lipid levels, most of them also need to take lipid-lowering medicines, in addition to the non-pharmacological treatments, such as reducing intake of dietary cholesterol, and increasing exercise.

It is currently recognized that hyperlipidemia includes hypercholesterolemia, hypertriglyceridemia, and complex hyperlipidemia (both of them are high). Therefore, according to the different pharmacological effects, the hypolipidemic medicines are divided into two major categories: mainly lowering cholesterol and mainly lowering triglycerides.

Most of the bilirubin in serum is derived from the hemoglobin produced by destruction of aged red blood cells. The glucuronidated bilirubin in the liver is called direct bilirubin, and the non-glucuronidated bilirubin in the liver is called indirect bilirubin. The sum of two bilirubins is total bilirubin.

Clinically, bilirubin testing is mainly used for diagnosis of liver diseases and biliary obstruction. When serum total bilirubin is greatly increased, human skin, eye sclera, urine and serum appear yellow, so that it is called jaundice or hyperbilirubinemia. When the liver is damaged by inflammation, necrosis, poisoning, etc., it can cause jaundice. Biliary tract disease and hemolytic disease can also cause jaundice. The mainly increased direct bilirubin is common in primary biliary cirrhosis, biliary obstruction and the like. The mainly increased indirect bilirubin is common in hemolytic diseases, neonatal jaundice or blood transfusion errors and the like. Both direct bilirubin and indirect bilirubin in patients with hepatitis and cirrhosis can be elevated. Increased total bilirubin can be seen in toxic or viral hepatitis, hemolytic jaundice, pernicious anemia, paroxysmal nocturnal hemoglobinuria, polycythemia, neonatal jaundice, internal hemorrhage, hemolytic jaundice after blood transfusion, acute yellow liver atrophy, abnormal congenital bilirubin metabolism (Crigler-Najjar syndrome, Gilbert syndrome, Dubin-Johnson syndrome), fructose intolerance and the like, and in subjects after intaking salicylic acid, erythromycin, rifampicin, progestin, novalgin and other medicines.

When bilirubin can not be normally converted into bile, pathological changes in hepatocytes, swelling of hepatocytes, compression of bile ducts in the liver, or obstruction of excretion of bile will increase bilirubin in the blood. Because bilirubin is a waste of heme metabolism in red blood cells in the blood, if the serum bilirubin is too high, it often indicates abnormal information such as liver lesions or bile duct obstruction. If the red blood cells are destroyed excessively, the indirect bilirubin is produced excessively, thus making the liver unable to completely convert it into direct bilirubin, and then hemolytic jaundice may occur. Meanwhile, the level of serum bilirubin represents the severity of abnormality.

Because of many causes of hyperbilirubinemia, the main treatment should be based on the causes. Only when the cause is eliminated, hyperbilirubinemia can be alleviated or subsided.

As the age increases, the function of the liver is gradually weakened. Usually this reduction does not cause jaundice, or abnormal indicators in liver function. Clinically, it is only manifested as high bilirubin. There are a large number of such middle-aged and elderly people who may have an age-related functional decline in liver and gall. There is currently no effective prevention or treatment for this group of people.

Due to the wide variety of hypolipidemic medicament, strong specificity and many adverse effects, there is an urgent need in the art to develop various medicament and functional foods capable of preventing and/or treating hyperlipidemia, and to develop medicament and/or functional foods capable of preventing and/or treating hyperbilirubinemia, which are positively significant for delaying aging and improving the quality of the elderly life.

SUMMARY OF INVENTION

The object of the present invention is to provide a medicament and/or a functional food for preventing and/or treating hyperlipemia.

Another object of the present invention is to provide a medicament and/or functional food for preventing and/or treating hyperbilirubinemia.

In the first aspect of the present invention, it provides a use of a compound of Formula (I) or a derivative of Formula (II) for preparation of a composition or a formulation for prevention and/or treatment of hyperlipidemia, $$A\text{-}NCS \qquad (I)$$

wherein in Formula (I):

NCS is an isothiocyanate group;

A is $-XR_1$ or $-CR_2R_3R_4$; wherein X is $-(CH_2)_n$-, and n is an integer of 0-6;

R1 is a methyl, t-butyl, isopropyl, methylthio, methoxy, allyl, methallyl, cyclohexyl, methylsulfinyl, naphthyl, methylcyclohexyl, morpholinyl, diethylamino, benzoyl, ethoxycarbonyl, t-octyl, chlorine atom, trimethylsilyl, or substituted or unsubstituted phenyl;

the term "substituted" means that one or more hydrogen atoms in a group are substituted by a substituent selected from the group consisting of halogen, methyl, bromomethyl, ethyl, methoxy, nitro, azido, trifluoromethyl, difluoromethoxy, methylthio, cyano, trifluoromethoxy, trifluoromethylthio, t-butoxycarbonyl, and ethoxycarbonyl;

each of R2, R3, and R4 is independently H, phenyl or C1-3 alkyl;

(II)

wherein in Formula (II):
A is as defined in Formula (I);
R5 is hydrogen, or a group connected to the carbon atom of via a sulphur atom and derived from a compound selected from the group consisting of N-acetylcysteine, glutathione, cysteine (C1-6 alkyl) ester, cysteinyl amino acid and cysteinyl amino acid (C1-6 alkyl) ester.

In another preferred embodiment, the amino acid is selected from glycine, glutamic acid, serine, alanine or methionine.

In another preferred embodiment, the compound of Formula (I) or the derivative of Formula (II) is selected from the group consisting of: isothiocyanates, adducts of isothiocyanate and N-acetyl cysteine, and a combination thereof; wherein the isothiocyanates are selected from the group consisting of: phenyl ethyl isothiocyanate, cyclohexyl isothiocyanate, 4-methoxybenzyl isothiocyanate, 4-chloro-benzyl isothiocyanate, phenylpropyl isothiocyanate, 4-phenyl-butyl isothiocyanate, 6-phenyl-hexyl isothiocyanate, triphenylmethyl isothiocyanate, 1-isothiocyanate-4-methanesulfonyl butane (sulforaphane), isothiocyanate α-methyl benzyl ester, hexyl isothiocyanate, isothiocyanate methyl cyclohexyl ester, 1-naphthyl isothiocyanate, 2-chlorophenyl isothiocyanate, 2-bromophenyl isothiocyanate, 3-chlorophenyl isothiocyanate, 3-bromophenyl isothiocyanate, 3-nitrophenyl isothiocyanate, 4-azido phenyl isothiocyanate, 4-fluorophenyl isothiocyanate, 4-chlorophenyl isothiocyanate, 4-bromophenyl isothiocyanate, 4-nitrophenyl isothiocyanate, ethoxycarbonyl isothiocyanate, tert-octyl isothiocyanate, p-tolyl isothiocyanate, benzoyl isothiocyanate, o-tolyl isothiocyanate, m-tolyl isothiocyanate, 2,3,4-trifluorophenyl isothiocyanate, 2,5-dimethoxyphenyl isothiocyanate, 2-(4-morpholino)ethyl isothiocyanate, 2-(trifluoromethyl)phenyl isothiocyanate, 2-(difluoromethoxy)phenyl isothiocyanate, 2-(methylthio)phenyl isothiocyanate, 2-fluoro-5-(trifluoromethyl)phenyl isothiocyanate, 3,5-bis (trifluoromethyl)phenyl isothiocyanate, 3-(4-morpholinyl)propyl isothiocyanate, 3-(trifluoromethyl)phenyl isothiocyanate, 3-(di-ethylamino)propyl isothiocyanate, 3-(methylthio)propyl isothiocyanate, 3-(methylthio)phenyl isothiocyanate, 3-cyano-phenyl isothiocyanate, 4-(trifluoromethyl)phenyl isothiocyanate, 4-(trifluoromethoxy)phenyl isothiocyanate, 4-(trifluoromethylthio)phenyl isothiocyanate, 4-(difluoromethoxy)phenyl isothiocyanate, 4-(methylthio)phenyl isothiocyanate, 4-cyano-phenyl isothiocyanate, 4-bromo-2-fluorophenyl isothiocyanate, 4-methoxy-phenyl isothiocyanate, methallyl isothiocyanate, ethyl 2-(4-isothiocyanato-phenoxy) toluenesulfonate, 2-chloro-ethyl isothiocyanate, 2-fluorophenyl isothiocyanate, 3-fluorophenyl isothiocyanate, butyl isothiocyanate, trimethylsilyl isothiocyanate, propyl isothiocyanate, ethyl isothiocyanate, tert-butyl isothiocyanate, isopropyl isothiocyanate, allyl isothiocyanate, methyl isothiocyanate, phenethyl isothiocyanate, benzyl isothiocyanate, phenyl isothiocyanate, 2,4,5-trichloro-phenyl isothiocyanate, 2,4,6-trichloro-phenyl isothiocyanate, 2,4-difluoro-phenyl isothiocyanate, 2,5-difluoro-phenyl isothiocyanate, 2,6-difluoro-phenyl isothiocyanate, 2,6-dimethyl-phenyl isothiocyanate, 2-ethyl-phenyl isothiocyanate, 2-chloro-4-nitrophenyl isothiocyanate, 3-methoxy-phenyl isothiocyanate, 4-(bromomethyl)phenyl isothiocyanate, 4-ethyl-phenyl isothiocyanate, 5-chloro-2-methyl-phenyl isothiocyanate, 1,4-dithioisocyanate-butane, 2-chloro-5-(trifluoromethyl)phenyl isothiocyanate, 2-methoxy-4-nitro-phenyl isothiocyanate, 3,4,5-trimethoxy-phenyl isothiocyanate, 3-(trifluoromethylthio)phenyl isothiocyanate, 4-chloro-3-(trifluoromethyl) phenyl isothiocyanate, 4-methyl-3-(trifluoromethyl)phenyl isothiocyanate, 2,3-dichloro-phenyl isothiocyanate, 2,4-dichloro-phenyl isothiocyanate, 2,5-dichloro-phenyl isothiocyanate, 2,6-dichloro-phenyl isothiocyanate, 2-(4-chlorophenyl)ethyl isothiocyanate, 2-(ethoxycarbonyl)phenyl isothiocyanate, 2-methoxy-5-methyl-phenyl isothiocyanate, 2-methoxy-phenyl thioisocyanate, 2-methoxyethyl thioisocyanate, 3,4-dichloro-phenyl isothiocyanate, 3,5-dichloro-phenyl isothiocyanate, 4-fluoro-3-(trifluoromethyl) phenyl isothiocyanate, 4-iodo-phenyl isothiocyanate, tert-butyl 3-isothiocyanato-benzoate, tert-butyl 4-isothiocyanato-benzoate, diphenyl-ethyl isothiocyanate.

Preferably, the isothiocyanates are selected from the group consisting of: isothiocyanates, adduct of isothiocyanate and N-acetyl cysteine, or combinations thereof; wherein the isothiocyanate is selected from the group: phenylethyl isothiocyanate, allyl isothiocyanate, benzyl isothiocyanate, phenyl isothiocyanate, L-ethyl phenyl isothiocyanate, cyclohexyl isothiocyanate, 4-methoxy benzyl isothiocyanate, 4-chloro-benzyl isothiocyanate, phenylpropyl isothiocyanate, 4-phenyl-butyl isothiocyanate, 6-phenyl-hexyl isothiocyanate, triphenylmethyl isothiocyanate, sulforaphane, and combinations thereof.

In another preferred embodiment, the compound of Formula (I) or the derivative of Formula (II) is selected from the group consisting of: phenylethyl isothiocyanate, allyl isothiocyanate, benzyl isothiocyanate, phenyl isothiocyanate, L-ethyl phenyl isothiocyanate, cyclohexyl isothiocyanate, 4-methoxy-benzyl isothiocyanate, 4-chloro-benzyl isothiocyanate, phenylpropyl isothiocyanate, 4-phenyl-butyl isothiocyanate, 6-hexyl benzene isothiocyanate, triphenylmethyl isothiocyanate, adduct of phenylethyl isothiocyanate and N-acetyl cysteine, sulforaphane, and combinations thereof.

In another preferred embodiment, the compound of Formula (I) or the derivative of Formula (II) is derived from animals and plants, chemical synthesis, or semi-chemical synthesis.

In another preferred embodiment, the composition is selected from the group consisting of: a pharmaceutical composition, a healthcare product composition, a food composition, a dietary supplement, and combinations thereof.

In another preferred embodiment, the composition is a pharmaceutical composition.

In another preferred embodiment, the medicament further comprises an additional component selected from the group consisting of: cholestyramine, colestipol, divistyramine, lovastatin, pravastatin, fluvastatin, simvastatin, atorvastatin, rosuvastatin, niacin, acipimox, inositol nicotinate, lifibrate, clofibrate, bezafibrate, fenofibrate, probucol, pantethine, elastase, timnodonic acid (EPA), docosahexaenoic acid (DHA), and combinations thereof.

In another preferred embodiment, the pharmaceutical composition comprises (a) a compound of Formula I, or a derivative of Formula II, and (b) a pharmaceutically acceptable carrier.

In another preferred embodiment, the component (a) is from 0.01 to 99.99% by weight, preferably from 0.1 to 90% by weight, and more preferably from 1 to 80% by weight, based on the total weight of the pharmaceutical composition.

In another preferred embodiment, the pharmaceutical composition is liquid, solid, or semi-solid.

In another preferred embodiment, the dosage form of the pharmaceutical composition comprises a tablet, a granule, a capsule, an oral solution, a pill, an ointment, an emulsion, a spray, an implant, a suppository, a cream or an injection.

In another preferred embodiment, the composition or formulation is used for (i) reducing the level of triglyceride in the serum of a mammal; (ii) reducing the level of low density lipoprotein in the serum of a mammal; and/or (iii) increasing the level of high density lipoprotein in the serum of a mammal.

In another preferred embodiment, the mammal comprises a human or a non-human mammal.

In another preferred embodiment, the non-human mammal comprises a rodent such as a mouse or a rat.

In another preferred embodiment, the mammal comprises a mammal suffering hyperlipidemia.

In another preferred embodiment, the composition is an oral preparation.

In another preferred embodiment, the composition (e.g., a pharmaceutical composition) is administered to a mammal via oral, injection, transdermal administration, intraluminal administration, or surgical injection.

In another preferred embodiment, the hyperlipidemia is selected from the group consisting of hypercholesterolemia, hypertriglyceridemia, complex hyperlipidemia, and combinations thereof.

In another preferred embodiment, the composition or formulation may be used alone or in combination in the prevention and/or treatment of hyperlipidemia.

In another preferred embodiment, the "used in combination" comprises: in combination with other medicines for preventing and/or treating hyperlipidemia.

In another preferred embodiment, the other drug for preventing and/or treating hyperlipidemia is selected from the group consisting of: cholestyramine, colestipol, divistyramine, lovastatin, pravastatin, fluvastatin, simvastatin, atorvastatin, rosuvastatin, niacin, acipimox, inositol nicotinate, lifibrate, clofibrate, bezafibrate, fenofibrate, probucol, pantethine, elastase, timnodonic acid (EPA), docosahexaenoic acid (DHA), and a combination thereof.

In another preferred embodiment, the composition or formulation is also used for the prevention and/or treatment of hyperbilirubinemia.

In another preferred embodiment, the composition or formulation is also used to reduce the level of total bilirubin in the serum of a mammal.

In another preferred embodiment, the mammal comprises a mammal having hyperbilirubinemia.

In another preferred embodiment, the hyperbilirubinemia is selected from the group consisting of: hemolytic jaundice, hepatic jaundice, cholestasis, gilbert syndrome, and a combination thereof.

In another preferred embodiment, the composition or formulation may be used alone or in combination in the use of preventing and/or treating hyperbilirubinemia.

In another preferred embodiment, the "used in combination with" comprises administration in combination with other medicines for preventing and/or treating hyperbilirubinemia.

In another preferred embodiment, the other medicines for preventing and/or treating hyperbilirubinemia are selected from the group consisting of: metacortandracin (prednisone), phenobarbital, ursodeoxycholic acid, S-ademetionine, methotrexate, azathioprine, cyclosporine, rifampicin, potassium magnesium aspartate, diammonium glycyrrhizinate, and combinations thereof.

In the second aspect of the present invention, it provides a pharmaceutical composition comprising:

(a1) a first active ingredient for treating hyperlipemia, which is a compound of Formula I, or a derivative of Formula II;

(a2) a second active ingredient for treating hyperlipemia, which is selected from other or additional medicines for preventing and/or treating hyperlipemia; and (b) a pharmaceutically acceptable carrier, wherein the compound of the Formula I or the derivative of the Formula II is as defined in the first aspect of the present invention.

In another preferred embodiment, the other medicines for preventing and/or treating hyperlipemia are selected from the group consisting of: statins, nicotinic acids, fibrates, bile acid sequestrants, omega-3 fatty acids, and combinations thereof.

In another preferred embodiment, the other medicines for preventing and/or treating hyperlipidemia are selected from the group consisting of: cholestyramine, colestipol, divistyramine, lovastatin, pravastatin, fluvastatin, simvastatin, atorvastatin, rosuvastatin, niacin, acipimox, inositol nicotinate, lifibrate, clofibrate, bezafibrate, fenofibrate, probucol, pantethine, elastase, timnodonic acid (EPA), docosahexaenoic acid (DHA), and combinations thereof.

In another preferred embodiment, the weight ratio of the first active ingredient to the second active ingredient is from 1:100 to 100:1, preferably from 1:10 to 10:1.

In another preferred embodiment, the weight percent of the first active ingredient and the second active ingredient is from 0.1% to 99%, preferably from 1% to 90%.

In another preferred embodiment, the pharmaceutical dosage form is an oral administration or a non-oral administration dosage form.

In another preferred embodiment, the oral administration dosage form is a tablet, a powder, a granule, a capsule, an emulsion, a syrup, a pill, or an oral solution.

In another preferred embodiment, the non-oral administration dosage form is an injection, an ampoule, a spray, an implant, a suppository, or a cream.

In another preferred embodiment, the concentration of the compound of the Formula I or the derivative of the Formula II is 0.001 mg-10000 mg/ml, preferably from 0.01 mg-1000 mg/ml, more preferably, 0.1 mg-500 mg/ml.

In the third aspect of the present invention, it provides a method for screening a drug candidate for treating hyperlipemia, which comprises the steps of:

(a) providing a test compound and a positive control compound, wherein the positive control compound is a compound of Formula I, or a derivative of Formula II; and (b) detecting the effect of the test compound on the triglyceride level in the non-human animal model in the test group, and comparing it with the corresponding experimental results in the positive control group and the negative control group, wherein, in the positive control group, the effect of the positive control compound on the level of triglyceride is detected;

wherein, if a decrease extent of triglyceride in the non-human animal model caused by the test compound is significantly higher than that in the negative control group, it indicates that the test compound is a drug candidate for treating hyperlipemia.

In another preferred embodiment, in step (b), the test group is compared with a positive control group and the ratio of V1 to V2 is compared, wherein V1 is a decrease extent V1 of the triglyceride in a non-human animal model caused by the test compound, whereas V2 is a decrease extent of the triglyceride in the non-human animal model caused by the positive control compound, wherein if V1/V2≥80%, the test compound is suggested to be a drug candidate for treating hyperlipemia.

In another preferred embodiment, the method further comprises the step (c): the test compound selected from the step (b) is further tested for its therapeutic effect on hyperlipemia.

In another preferred embodiment, the term "significantly higher" means V1/V0≥2, preferably ≥3, and more preferably ≥4, wherein, V1 is a decrease extent in a non-human animal model with hyperlipidemia caused by the test compound; and V0 is a decrease extent in a non-human animal model with hyperlipidemia in a negative control group (or model group).

In another preferred embodiment, the method is non-diagnostic and non-therapeutic method.

In the fourth aspect of the present invention, it provides a method of treating hyperlipemia, comprising the steps of administering a compound of Formula I or a derivative of Formula II to a mammal in need thereof, wherein the compound of Formula I or the derivative of Formula II is as defined in the first aspect of the present invention.

In another preferred embodiment, the mammal comprises a mammal suffering hyperlipidemia.

In another preferred embodiment, the hyperlipidemia is selected from the group consisting of hypercholesterolemia, hypertriglyceridemia, complex hyperlipidemia, and combinations thereof.

In another preferred embodiment, the mammal comprises a human.

In another preferred embodiment, the mammal comprises a non-human mammal.

In another preferred embodiment, the mammal comprises a rodent such as a rat or a mouse.

In another preferred embodiment, the administration dose is 0.01-100 mg/kg/day, preferably 0.1-50 mg/kg/day, and more preferably 0.5-20 mg/kg/day.

In another preferred embodiment, the administration frequency is 1-5 times/day, preferably 1-3 times/day.

In another preferred embodiment, the administration comprises one or more cycles, and each cycle is 2-60 days, preferably 7-30 days.

In the fifth aspect of the present invention, it provides an in vitro non-therapeutic method for reduction of mammalian triglyceride levels, comprising a step of administering to a mammal in need thereof a compound of Formula I or a derivative of Formula II, wherein the compound of Formula I or the derivative of Formula II is as defined in the first aspect of the present invention.

In another preferred embodiment, the mammal comprises a mammal suffering hyperlipidemia.

In another preferred embodiment, the mammal comprises a human.

In another preferred embodiment, the mammal comprises a non-human mammal.

In another preferred embodiment, the mammal comprises a rodent such as a rat or a mouse.

In another preferred embodiment, the administration dose is 0.01-100 mg/kg/day, preferably 0.1-50 mg/kg/day, and more preferably 0.5-20 mg/kg/day.

In another preferred embodiment, the administration frequency is 1-5 times/day, preferably 1-3 times/day.

In another preferred embodiment, the administration comprises one or more cycles, and each cycle is 2-60 days, preferably 7-30 days.

In the sixth aspect of the present invention, it provides a use of a compound of Formula (I) or a derivative of Formula (II) for preparation of a composition or a formulation for prevention and/or treatment of hyperbilirubinemia, $$\text{A-NCS} \qquad (I)$$

wherein in Formula (I):

NCS is an isothiocyanate group;

A is —XR1 or —CR2R3R4; wherein X is —(CH2)n-, and n is an integer of 0-6;

R1 is a methyl, t-butyl, isopropyl, methylthio, methoxy, allyl, methallyl, cyclohexyl, methylsulfinyl, naphthyl, methylcyclohexyl, morpholinyl, diethylamino, benzoyl, ethoxycarbonyl, t-octyl, chlorine atom, trimethylsilyl, or substituted or unsubstituted phenyl;

the term "substituted" means that one or more hydrogen atoms in a group are substituted by a substituent selected from the group consisting of halogen, methyl, bromomethyl, ethyl, methoxy, nitro, azido, trifluoromethyl, difluoromethoxy, methylthio, cyano, trifluoromethoxy, trifluoromethylthio, t-butoxycarbonyl, and ethoxycarbonyl;

each of R2, R3, and R4 is independently H, phenyl or C1-3 alkyl;

(II)

wherein in Formula (II):

A is defined as in Formula (I);

R5 is hydrogen, or a group connected to the carbon atom of via a sulphur atom and derived from a compound selected from the group consisting of: N-acetylcysteine, glutathione, cysteine (C1-6 alkyl) ester, cysteinyl amino acid and cysteinyl amino acid (C1-6 alkyl) ester.

In another preferred embodiment, the pharmaceutical composition further comprises additional medicines for preventing and/or treating hyperbilirubinemia which are selected from the group consisting of: metacortandracin (prednisone), phenobarbital, ursodeoxycholic acid, S-ademetionine, methotrexate, azathioprine, cyclosporine, rifampicin, potassium magnesium aspartate, diammonium glycyrrhizinate, and combination thereof.

In another preferred embodiment, the pharmaceutical composition comprises (a) a compound of Formula I, or a derivative of Formula II, and (b) a pharmaceutically acceptable carrier.

In another preferred embodiment, the component (a) is from 0.01 to 99.99% by weight, preferably from 0.1 to 99.9% by weight, more preferably from 0.1% to 99% by weight, based on the total weight of the pharmaceutical composition.

In the seventh aspect of the present invention, it provides a pharmaceutical composition, comprising:

(a1) a first active ingredient for treating hyperbilirubinemia, which is a compound of Formula I, a derivative of Formula II;

(a2) a second active ingredient for treating hyperbilirubinemia, which is selected from other or additional medicine for preventing and/or treating hyperbilirubinemia; and (b) a pharmaceutically acceptable carrier, wherein the compound of the Formula I or the derivative of the Formula II is as defined in the sixth aspect of the present invention.

In another preferred embodiment, the other or additional medicines for preventing and/or treating hyperbilirubinemia are selected from the group consisting of: metacortandracin (prednisone), phenobarbital, ursodeoxycholic acid, S-ademetionine, methotrexate, azathioprine, cyclosporine, rifampicin, potassium magnesium aspartate, diammonium glycyrrhizinate, and combinations thereof.

In another preferred embodiment, the weight ratio of the first active ingredient to the second active ingredient is from 1:100 to 100:1, preferably from 1:10 to 10:1.

In another preferred embodiment, the weight percent of the first active ingredient and the second active ingredient is from 0.1% to 99%, preferably from 1% to 90%.

In another preferred embodiment, the concentration of the compound of the Formula I or the derivative of the Formula II is 0.001 mg-10000 mg/ml, preferably from 0.01 mg-1000 mg/ml, and more preferably 0.1 mg-500 mg/ml.

In the eighth aspect of the present invention, it provides a method for screening a drug candidate for treating hyperbilirubinemia, comprising the steps of:

(a) providing a test compound and a positive control compound, wherein the positive control compound is a compound of Formula I, or a derivative of Formula II; and (b) detecting the effect of the test compound on the total bilirubin level in the non-human animal model in the test group and comparing it with the corresponding experimental results in the positive control group and the negative control group, wherein, in the positive control group, the effect of the positive control compound on the level of total bilirubin is detected;

wherein, if the decrease degree of total bilirubin in the non-human animal model caused by the test compound is significantly higher than that in the negative control group, it indicates that the test compound is a drug candidate for treating hyperbilirubinemia.

In another preferred embodiment, in step (b), the test group is compared with a positive control group and the ratio of V1 to V2 is compared, wherein V1 is a decrease extent V1 of the total bilirubin in a non-human animal model caused by the test compound, whereas V2 is a decrease extent of the total bilirubin in the non-human animal model caused by the positive control compound, wherein if V1/V2≥80%, the test compound is suggested to be a drug candidate for treating hyperbilirubinemia.

In another preferred embodiment, the method further comprises the step (c): the test compound selected from the step (b) is further tested for its therapeutic effect on hyperbilirubinemia.

In another preferred embodiment, the term "significantly higher" means V1/V0≥2, preferably ≥3, and more preferably ≥4, wherein, V1 is a decrease extent of total bilirubin in a non-human animal model caused by the test compound; and V0 is a decrease extent of total bilirubin in a non-human animal model in a negative control group (or model group).

In another preferred embodiment, the method is non-diagnostic and non-therapeutic method.

In the ninth aspect of the present invention, it provides a method of treating hyperbilirubinemia, comprising a step of administering a compound of Formula I or a derivative of Formula II to a mammal in need thereof, wherein the compound of Formula I or the derivative of Formula II is as defined in the sixth aspect of the present invention.

In another preferred embodiment, the mammal comprises a mammal suffering hyperbilirubinemia.

In another preferred embodiment, the hyperbilirubinemia is selected from the group consisting of hemolytic jaundice, hepatic jaundice, cholestasis, gilbert syndrome, and combinations thereof.

In another preferred embodiment, the mammal comprises a human.

In another preferred embodiment, the mammal comprises a non-human mammal.

In another preferred embodiment, the mammal comprises a rodent such as a rat or a mouse.

In another preferred embodiment, the administration dose is 0.01-100 mg/kg/day, preferably 0.1-50 mg/kg/day, and more preferably 0.5-20 mg/kg/day.

In another preferred embodiment, the administration frequency is 1-5 times/day, preferably 1-3 times/day.

In another preferred embodiment, the administration comprises one or more cycles, and each cycle is 2-60 days, preferably 7-30 days.

In the tenth aspect of the present invention, it provides an in vitro non-therapeutic method for the reduction of mammalian total bilirubin levels, comprising a step of administering to a mammal in need thereof a compound of Formula I or a derivative of Formula II, wherein the compound of Formula I or the derivative of Formula II is as defined in the sixth aspect of the present invention.

In another preferred embodiment, the mammal comprises a mammal having hyperbilirubinemia.

In another preferred embodiment, the mammal comprises a human.

In another preferred embodiment, the mammal comprises a non-human mammal.

In another preferred embodiment, the mammal comprises a rodent such as a rat or a mouse.

In another preferred embodiment, the administration dose is 0.01-100 mg/kg/day, preferably 0.1-50 mg/kg/day, and more preferably 0.5-20 mg/kg/day.

In another preferred embodiment, the administration frequency is 1-5 times/day, preferably 1-3 times/day.

In another preferred embodiment, the administration comprises one or more cycles, and each cycle is 2-60 days, preferably 7-30 days.

It should be understood that, within the scope of the present invention, each technical feature of the present invention described above and in the following (as examples) may be combined with each other to form a new or preferred technical solution, which is not listed here due to space limitations.

DESCRIPTION OF FIGURE

FIG. 2 shows high-density lipoprotein levels in serum are significantly elevated in the administration group (Group A, Group B, and Group D) compared with baseline. The order of the increase is as follows: Group A (group with the administration of 30 mg)<Group B ((group with the administration of 90 mg)<Group D ((group with the administration of 60 mg); and levels of high-density lipoprotein in serum in the Group C (0 mg group) are significantly decreased. Compared with Group C, the low-density cholesterol levels of the administration group (Group A, Group B, and Group D) are decreased significantly by −0.88%, 6.92%, and 0.05%, respectively, and the decline in Group A is most significant. Compared with Group C, the triglyceride levels are significantly decreased before and after administration in the administration Group (Group A, Group B, and Group D), with the most significant decrease in Group B and Group D.

DETAILED DESCRIPTION

After extensive and intensive researches, the present inventors have firstly discovered that isothiocyanate compounds and derivatives thereof (compounds of Formula I, Formula II), after administered to patients with benign prostatic hyperplasia, can be effectively used not only for (i) preventing and/or treating hyperlipidemia; (ii) lowering triglyceride levels in mammals; (iii) lowering low density lipoprotein levels in mammals; and/or (iv) increasing high density lipoprotein levels in mammals. It is unexpectedly found that the compounds can significantly lower the total bilirubin level in serum of a patient with benign prostatic hyperplasia, and it is unexpectedly found that isothiocyanate compounds and their derivatives (compounds of Formula I, Formula II) can be effectively used not only for (i) preventing and/or treating hyperbilirubinemia; (ii) reducing total bilirubin levels in mammalian serum. On the basis of this discovery, the present inventors have completed the present invention.

Active Ingredient

The active ingredient according to the present invention is an isothiocyanate compound or a derivative thereof, and the active ingredient is a compound of Formula (I) or a derivative of Formula (II), or a combination thereof:

$$A\text{-NCS} \quad (I)$$

wherein in Formula (I):

NCS is an isothiocyanate group;

A is —XR1 or —CR2R3R4; wherein X is —(CH2)n-, and n is an integer of 0-6;

R1 is a methyl, t-butyl, isopropyl, methylthio, methoxy, allyl, methallyl, cyclohexyl, methylsulfinyl, naphthyl, methyl cyclohexyl, morpholinyl, diethylamino, benzoyl, ethoxycarbonyl, t-octyl, chlorine atom, trimethylsilyl, or substituted or unsubstituted phenyl;

the term "substituted" means that one or more hydrogen atoms in a group are substituted by a substituent selected from the group consisting of halogen, methyl, bromomethyl, ethyl, methoxy, nitro, azido, trifluoromethyl, difluoromethoxy, methylthio, cyano, trifluoromethoxy, trifluoromethylthio, t-butoxycarbonyl, and ethoxycarbonyl;

each of R2, R3, and R4 is independently H, phenyl or C1-3 alkyl;

(II)

wherein in Formula (II):

A is as defined in Formula (I);

R5 is hydrogen, or a group connected to the carbon atom of via a sulphur atom and derived from a compound selected from the group consisting of: N-acetylcysteine, glutathione, cysteine (C1-6 alkyl) ester, cysteinyl amino acid and cysteinyl amino acid (C1-6 alkyl) ester.

In another preferred embodiment, the amino acid is selected from glycine, glutamic acid, serine, alanine or methionine.

A preferred class of active ingredients are selected from the group consisting of: an isothiocyanate, an adduct of isothiocyanate and N-acetyl cysteine, and combinations thereof;

wherein the isothiocyanate is selected from the group consisting of: phenylethyl isothiocyanate, cyclohexyl isothiocyanate, 4-methoxybenzyl isothiocyanate, 4-chloro-benzyl isothiocyanate, phenylpropyl isothiocyanate, 4-phenylbutyl isothiocyanate, 6-phenyl-hexyl isothiocyanate, triphenylmethyl isothiocyanate, 1-isothiocyanate-4-methanesulfonyl butane (sulforaphane), isothiocyanate α-methyl benzyl ester, hexyl isothiocyanate, isothiocyanate methyl cyclohexyl ester, 1-naphthyl isothiocyanate, 2-chlorophenyl isothiocyanate, 2-bromophenyl isothiocyanate, 3-chlorophenyl isothiocyanate, 3-bromophenyl isothiocyanate, 3-nitrophenyl isothiocyanate, 4-azido phenyl isothiocyanate, 4-fluorophenyl isothiocyanate, 4-chlorophenyl isothiocyanate, 4-bromophenyl isothiocyanate, 4-nitrophenyl isothiocyanate, ethoxycarbonyl isothiocyanate, tert-octyl isothiocyanate, p-tolyl isothiocyanate, benzoyl isothiocyanate, o-tolyl isothiocyanate, m-tolyl isothiocyanate, 2,3,4-trifluorophenyl isothiocyanate, 2,5-dimethoxyphenyl isothiocyanate, 2-(4-morpholino)ethyl isothiocyanate, 2-(trifluoromethyl)phenyl isothiocyanate, 2-(difluoromethoxy)phenyl isothiocyanate, 2-(methylthio)phenyl isothiocyanate, 2-fluoro-5-(trifluoromethyl)phenyl isothiocyanate, 3,5-bis(trifluoromethyl)phenyl isothiocyanate, 3-(4-morpholinyl)propyl isothiocyanate, 3-(trifluoromethyl)phenyl isothiocyanate, 3-(di-ethylamino)propyl isothiocyanate, 3-(methylthio)propyl isothiocyanate, 3-(methylthio)phenyl isothiocyanate, 3-cyano-phenyl isothiocyanate, 4-(trifluoromethyl)phenyl isothiocyanate, 4-(trifluoromethoxy)phenyl isothiocyanate, 4-(trifluoromethylthio)phenyl isothiocyanate, 4-(difluoromethoxy)phenyl isothiocyanate, 4-(methylthio)phenyl isothiocyanate, 4-cyano-phenyl isothiocyanate, 4-bromo-2-fluorophenyl isothiocyanate, 4-methoxy-phenyl isothiocyanate, methallyl isothiocyanate, ethyl 2-(4-isothiocyanato-phenoxy) toluenesulfonate, 2-chloro-ethyl isothiocyanate, 2-fluorophenyl isothiocyanate, 3-fluorophenyl isothiocyanate, butyl isothiocyanate, trimethylsilyl isothiocyanate, propyl isothiocyanate, ethyl isothiocyanate, tert-butyl isothiocyanate, isopropyl isothiocyanate, allyl isothiocyanate, methyl isothiocyanate, phenethyl isothiocyanate, benzyl isothiocyanate, phenyl isothiocyanate, 2,4,5-trichloro-phenyl isothiocyanate, 2,4,6-trichloro-phenyl isothiocyanate, 2,4-difluoro-phenyl isothiocyanate, 2,5-difluoro-phenyl isothiocyanate, 2,6-difluoro-phenyl isothiocyanate, 2,6-dimethyl-phenyl isothiocyanate, 2-ethyl-phenyl isothiocyanate, 2-chloro-4-nitro-phenyl isothiocyanate, 3-methoxy-phenyl isothiocyanate, 4-(bromomethyl)phenyl isothiocyanate, 4-ethyl-phenyl isothiocyanate, 5-chloro-2-methyl-phenyl isothiocyanate, 1,4-dithioisocyanate-butane, 2-chloro-5-(trifluoromethyl)phenyl isothiocyanate, 2-methoxy-4-nitro-phenyl isothiocyanate, 3,4,5-trimethoxy-phenyl isothiocyanate, 3-(trifluoromethylthio)phenyl isothiocyanate, 4-chloro-3-(trifluoromethyl)phenyl isothiocyanate, 4-methyl-3-(trifluoromethyl)phenyl isothiocyanate, 2,3-dichloro-phenyl isothiocyanate, 2,4-dichloro-phenyl isothiocyanate, 2,5-dichloro-phenyl isothiocyanate, 2,6-dichloro-phenyl isothiocyanate, 2-(4-chlorophenyl)ethyl isothiocyanate, 2-(ethoxycarbonyl)phenyl isothiocyanate, 2-methoxy-5-methyl-phenyl isothiocyanate, 2-methoxy-phenyl thioisocyanate, 2-methoxyethyl thioisocyanate, 3,4-dichloro-phenyl isothiocyanate, 3,5-dichloro-phenyl isothiocyanate, 4-fluoro-3-(trifluoromethyl) phenyl isothiocyanate, 4-iodo-phenyl isothiocyanate, tert-butyl 3-isothiocyanato-benzoate, tert-butyl 4-isothiocyanato-benzoate, diphenyl-ethyl isothiocyanate Preferably, the isothiocyanates are selected from the group consisting of: isothiocyanates, adduct of isothiocyanate and N-acetyl cysteine, or combinations thereof;

wherein the isothiocyanate is selected from the group: phenylethyl isothiocyanate, allyl isothiocyanate, benzyl isothiocyanate, phenyl isothiocyanate, L-ethyl phenyl isothiocyanate, cyclohexyl isothiocyanate, 4-methoxy benzyl isothiocyanate, 4-chloro-benzyl isothiocyanate, phenylpropyl isothiocyanate, 4-phenyl-butyl isothiocyanate, 6-phenylhexyl isothiocyanate, triphenylmethyl isothiocyanates, sulforaphane, and combinations thereof.

In another preferred embodiment, the compound of Formula (I) or the derivative of Formula (II) is selected from the group consisting of: phenylethyl isothiocyanate, allyl isothiocyanate, benzyl isothiocyanate, phenyl isothiocyanate, L-ethyl phenyl isothiocyanate, cyclohexyl isothiocyanate, 4-methoxy-benzyl isothiocyanate, 4-chloro-benzyl isothiocyanate, phenylpropyl isothiocyanate, 4-phenyl-butyl isothiocyanate, 6-hexyl benzene isothiocyanate, triphenylmethyl isothiocyanate, adduct of phenethyl isothiocyanate and N-acetyl cysteine adduct, sulforaphane, and combinations thereof.

The above isothiocyanate compound or a derivative thereof may be used alone or in combination by using two or more compounds, and when used in combination, there is no particular limitation mass ratio of each compound, as long as the therapeutic purpose is achieved.

In the present invention, there is no particular limitation on the method for obtaining an isothiocyanate compound. For example, it can be extracted from natural plants (for example, leaf mustard or radish), prepared by chemical synthesis or semi-chemical synthesis, and the like. The isothiocyanate compounds used in the present invention are commercially available, for example, from Sigma-Aldrich.

Composition and the Use Thereof

The isothiocyanate compound or a derivative thereof (the compound of Formula I, the derivative of Formula II) of the present invention and the composition containing the compound of the present invention as a main active ingredient can be used for treatment, prevention, and alleviation of hyperlipidemia, and can also be used for the treatment, prevention, and alleviation of hyperbilirubinemia.

The compositions of the invention include, but are not limited to, pharmaceutical compositions, food compositions, healthcare product compositions, dietary supplements, and the like.

The pharmaceutical composition of the present invention comprises a safe and effective amount of an isothiocyanate compound or a derivative thereof (a compound of Formula I, a derivative of Formula II), and a pharmaceutically acceptable excipient or carrier. The term "safe and effective amount" means that the amount of the compound is sufficient to significantly improve the condition without causing serious side effects. In general, the pharmaceutical composition contains 0.1 to 1000 mg of an isothiocyanate compound per dose, more preferably 1 to 500 mg of an isothiocyanate compound per dose, and most preferably 2 to 300 mg of isothiocyanate per dose. Preferably, the "one dose" is a capsule or tablet.

The term "pharmaceutically acceptable carrier" means one or more compatible solid or liquid fillers or gel materials which are suitable for human use and which must be of sufficient purity and of sufficiently low toxicity. As used herein, "compatibility" means that each component in the composition is capable of blending with the compounds of the present invention and with each other without significantly reducing the pharmacodynamic effect of the compound. Examples of pharmaceutically acceptable carriers are cellulose and its derivatives (such as sodium carboxymethylcellulose, sodium ethylcellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerin, mannitol, sorbitol, etc.), emulsifiers (such as Tween®), wetting agent (such as sodium lauryl sulfate), colorants, flavoring agents, stabilizers, antioxidants, preservatives, pyrogen-free water, and the like.

The mode of administration of the compound or pharmaceutical composition of the present invention is not particularly limited, and the representative modes of administration include, but are not limited to, oral, rectum, parenteral (intravenous, intramuscular or subcutaneous), and topical administration. Preferably, the mode of administration is oral administration.

Solid formulations for oral administration include capsules, tablets, pills, powders, and granules. In these solid formulations, the active compound is mixed with at least one conventional inert excipient (or carrier), such as sodium citrate or dicalcium phosphate, or mixed with the following components: (a) fillers or solubilizers, for example, starch, lactose, sucrose, glucose, mannitol and silicic acid; (b) binders such as hydroxymethylcellulose, alginates, gelatin, polyvinylpyrrolidone, sucrose and arabic gum; (c) humectants, for example, glycerin; (d) disintegrants such as agar, calcium carbonate, potato starch or tapioca starch, alginic acid, certain complex silicates, and sodium carbonate; (e) slow solvents such as paraffin; (f) absorbing accelerators, for example, quaternary amine compounds; (g) wetting agents, such as cetyl alcohol and glyceryl monostearate; (h) adsorbents, for example, kaolin; and (i) lubricants, for example, talc, calcium stearate, magnesium stearate, solid polyethylene glycol, sodium lauryl sulfate, or a mixture thereof. In capsules, tablets and pills, the formulation may also contain a buffer.

Solid formulations such as tablets, sugar pills, capsules, pills, and granules can be prepared with coatings and shells such as enteric coatings and other materials known in the art. They may contain opacifying agents and the release of the active compound or compound in such compositions may be released in a portion of the digestive tract in a delayed manner. Examples of embedding components that can be employed are polymeric materials and waxy materials. If necessary, the active compound may also be in microencapsulated form with one or more of the above-mentioned excipients.

Liquid formulations for oral administration include pharmaceutically acceptable emulsions, solutions, suspensions, syrups or elixirs. In addition to the active compound, the liquid formulation may contain inert diluents conventionally employed in the art, such as water or other solvents, solubilizers and emulsifiers, e.g., ethanol, isopropanol, ethyl carbonate, ethyl acetate, propylene glycol, 1,3-butanediol, dimethylformamide and oils, and especially cottonseed oil, peanut oil, corn germ oil, olive oil, castor oil and sesame oil or a mixture thereof.

In addition to these inert diluents, the compositions may contain adjuvants such as wetting agents, emulsifying and suspending agents, sweetening agents, flavoring agents, and fragrance.

In addition to the active compound, the suspension may contain suspending agents, for example, ethoxylated isostearyl alcohol, polyoxyethylene sorbitol and sorbitan esters, microcrystalline cellulose, aluminum methoxide and agar, or mixtures thereof.

Compositions for parenteral injection may comprise a physiologically acceptable sterile aqueous or nonaqueous solution, dispersion, suspension or emulsion, and sterile powder for reconstitution into sterile injectable solutions or dispersions. Suitable aqueous and nonaqueous vehicles, diluents, solvents or excipients include water, ethanol, polyols and suitable mixtures thereof.

Dosage forms for the compounds of the present invention for topical administration include ointments, powders, patches, propellants and inhalants. The active ingredient is mixed with a physiologically acceptable carrier and any preservatives, buffers, or propellants which may be required if necessary under sterile conditions.

The compounds of the present invention may be administered alone or in combination with other pharmaceutically acceptable compounds (e.g., other medicines that prevent and/or treat hyperlipidemia or hyperbilirubinemia).

When a pharmaceutical composition is used, a safe and effective amount of a compound of the present invention is administered to a mammal (e.g., a human) in need of treatment, wherein the dose at the time of administration is a pharmaceutically acceptable effective administration dose, for a human with 60 kg body weight, the daily dose is usually 0.1 to 1000 mg, preferably 1 to 600 mg, and more preferably 2 to 300 mg. Of course, the specific doses should also determined after factors such as the route of administration, the health condition of the patient, etc. are considered, which are within the skills of the skilled physician.

Triglyceride and Lipoprotein Cholesterol

When blood triglyceride (TG) and/or low-density lipoprotein cholesterol (LDL-C) is too high or high-density lipoprotein cholesterol (HDL-C) is too low, it is called dyslipidemia in modern medicine.

In the present invention, the levels of triglyceride (TG) and/or low density lipoprotein cholesterol (LDL-C) or high density lipoprotein cholesterol (HDL-C) in serum of a mammal (such as a human) is detected, thereby judging the effectiveness of the isothiocyanate compound or derivatives thereof (the compound of Formula I or the derivative of Formula II) on the treatment of dyslipidemia.

Total Bilirubin

Total bilirubin (TBIL) is the sum of both direct bilirubin and indirect bilirubin. Most of the bilirubin in serum is derived from the hemoglobin produced by the destruction of aged red blood cells. The glucuronidated bilirubin in the liver is called direct bilirubin, and non-glucuronidated bilirubin in the liver is called indirect bilirubin.

In the present invention, the effectiveness of the isothiocyanate compound or its derivative (the compound of the Formula I, the derivative of the Formula II) on the treatment of hyperbilirubinemia is judged by detecting the level of total bilirubin in serum of a mammal (such as a human).

In a preferred embodiment, when the level of total bilirubin in the serum of a mammal (e.g., a human) is significantly reduced, it indicates that an isothiocyanate compound or a derivative thereof (a compound of Formula I, a derivative of the Formula II) has a therapeutic effect on hyperbilirubinemia.

Method for Lowering Triglyceride

In another preferred embodiment, the method comprises ingesting a pharmaceutical composition of the present invention, a food composition of the present invention, or combinations thereof. The subject is a human.

In another preferred embodiment, the method comprises ingesting a pharmaceutical composition of the present invention, a food composition of the present invention, or combinations thereof. The subject is an animal, preferably a mouse, or a rabbit.

Method of Reducing Total Bilirubin

In another preferred embodiment, the method comprises ingesting a pharmaceutical composition of the present invention, a food composition of the present invention, or combinations thereof. The subject is a human.

In another preferred embodiment, the method comprises ingesting a pharmaceutical composition of the present invention, a food composition of the present invention, or combinations thereof. The subject is an animal, preferably a mouse, or a rabbit.

The main advantages of the present invention include:

(1) The present inventors have found for the first time that isothiocyanate compounds or derivatives thereof (a compound of Formula I or a derivative of Formula II) have an activity of preventing and/or treating hyperlipemia.

(2) The present inventors have found for the first time that isothiocyanate compounds or derivatives thereof (a compound of Formula I, a derivative of Formula II) are capable of (i) significantly reducing triglycerides and low density lipoprotein level in mammals; and/or (ii) significantly increasing high density lipoprotein levels in mammals.

(3) The present inventors have found for the first time that isothiocyanate compounds or derivatives thereof (a compound of Formula I or a derivative of Formula II) can prevent and/or treat hyperlipemia, and has unexpectedly found that they can also prevent and/or treat hyperbilirubinemia.

(4) The present inventors have found for the first time that isothiocyanate compounds or derivatives thereof (a compound of the Formula I or a derivative of the Formula II) can significantly lower the bilirubin level in a mammal.

(5) The present inventors have found for the first time that isothiocyanate compounds or derivative thereof (a compound of Formula I or a derivative of Formula II) have an activity of preventing and/or treating hyperbilirubinemia.

(6) The present inventors have found for the first time that isothiocyanate compounds or derivatives thereof (a compound of Formula I or a derivative of Formula II) can significantly lower total bilirubin level in mammalian serum.

The present invention is further described below with reference to specific embodiments. It should be understood that these examples are only for illustrating the present invention and not intended to limit the scope of the present invention. The conditions of the experimental methods not specifically indicated in the following examples are usually in accordance with conventional conditions, or according to the manufacturer's proposed conditions. Unless otherwise stated, percentages and parts are by weight and parts by weight. In the following examples, it is deemed as having statistically significant difference if it is $*p<0.05$, $**p<0.01$ vs baseline.

Example 1 Study on Hypolipidemic Activity in Rats

Materials and Methods:

Reagent: phenylethyl isothiocyanate, synthesized by Wuxi Jiexi Pharmaceutical Technology Co., Ltd. The chemical construction was determined by NMR, UV, IR, MS, etc., and its content and purity were determined by HPLC (>99%); Fulinmen Brand corn oil, manufactured by Dongliang Industry (Zhangjiagang) Co., Ltd.

Animals: Clean SD rats, half male and half female, weighed 80-100 g, were provided by Shanghai Slac Laboratory Animal Co., Ltd. Free access to drinking water, ambient temperature of 20-25° C., relative humidity of 40%-70%.

Experimental methods: Male rats with 123-149 g of body weight were randomly divided into 4 groups according to their body weights. Female rats with 116-142 g of body weight were randomly divided into 4 groups according to body weights. In the control group and high dose group, there were 60 in each group. In the medium-dose and low-dose groups, there were 40 in each group, half male and half female. 0, 20, 60, 120 mg/kg of phenethyl isothiocyanate was administered by oral gavage, wherein the test drug was diluted with corn oil. The rats were administered continuously for 6 months, and administered 6 days a week, and administered at the same time every morning.

Observation items: blood biochemical examination.

The experimental results were shown in Table 1.

TABLE 1

Effect of phenylethyl isothiocyanate on serum triglyceride (TG) levels in rats (at terminal of administration, $\bar{x} \pm SD$) n = 14

| gender | dosage(mg/kg) | TG(mmol/L) |
|---|---|---|
| male | 0 | 2.28 ± 0.67 |
| | 20 | 1.73 ± 0.79* |
| | 60 | 1.27 ± 0.38** |
| | 120 | 1.00 ± 0.22** |
| female | 0 | 2.86 ± 1.49 |
| | 20 | 2.13 ± 0.82* |
| | 60 | 1.68 ± 0.63** |
| | 120 | 1.35 ± 0.72** |

Note:
*$p < 0.05$ as compared to the 0 mg/kg group;
**$p < 0.01$ as compared to the 0 mg/kg group.

Results and Discussion:

The results showed that the TG level in the 20 mg/kg group of the female rats was lower than that in the 0 mg/kg group ($p<0.05$), and the TG levels in the 60 mg/kg and 120 mg/kg groups were significantly lower than that in the 0 mg/kg group ($p<0.01$). The TG level in the 20 mg/kg group of the male rats was lower than that in the 0 mg/kg group ($p<0.05$), and the TG levels in the 60 mg/kg and 120 mg/kg groups were significantly lower than that in the 0 mg/kg group ($p<0.01$).

Figure 1:
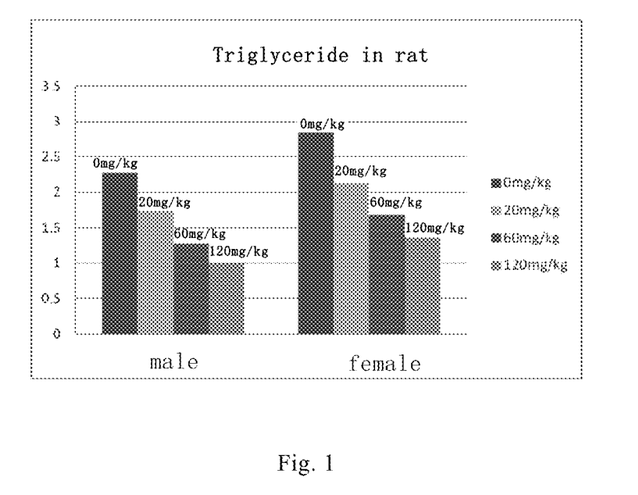
FIG. 1 shows that compared with the 0 mg/kg group, in the 20 mg/kg, 60 mg/kg, and 120 mg/kg dose groups of female rats and male rats, the triglycerides in the serum are significantly decreased and dose-related.

The results are shown in FIG. 1. Compared with the 0 mg/kg group, the levels of triglycerides in serum in the 20 mg/kg, 60 mg/kg, and 120 mg/kg dose groups of female rats and male rats were significantly lower and were dose-dependent, that is, there was a significant decrease extent in the concentration of triglycerides in serum as the concentration of administration was increased. Compared with the 0 mg/kg group, the triglycerides in the serum of the 20 mg/kg, 60 mg/kg, and 120 mg/kg dose groups of female rats were significantly decreased by 25.5%, 41.2%, and 52.8%, respectively; and the triglycerides in the serum of the 20 mg/kg, 60 mg/kg, and 120 mg/kg dose groups of male rats were significantly reduced by 24.1%, 44.3%, and 56.1%, respectively.

The results showed that after the clean SD rats were fed with the isothiocyanate compound of the present invention (such as phenylethyl isothiocyanate) for 6 months, the phenylethyl isothiocyanate significantly reduced the triglyceride levels in serum of the rats.

Example 2: Study on Hypolipidemic and Total Bilirubin Activity in Patients with Benign Prostatic Hyperplasia Objective:

To study the clinical efficacy and safety of oral phenylethyl isothiocyanate capsules on the treatment of benign prostatic hyperplasia (BPH).

Experimental Design:

A multicenter, randomized, double-blind, placebo parallel control design was used to preliminarily evaluate the safety and efficacy of phenylethyl isothiocyanate capsules on the treatment of BPH patients.

Subjects meeting the entry criteria were randomly assigned to any of the following four groups at a ratio of 1:1:1:1: administration group (Group A): phenylethyl isothiocyanate 10 mg/time, 3 times a day; administration group (group D): phenylethyl isothiocyanate 20 mg/time, 3 times a day; administration group (group B): phenylethyl isothiocyanate 30 mg/time, 3 times a day; placebo group (group C):

phenylethyl isothiocyanate placebo 1 capsule/time, 3 times a day. Oral administration was continued for 24 weeks.

Research Base:

4 hospitals in Beijing, 4 hospitals in Shanghai, and 6 hospitals in Jiangsu.

Experimental Participants:

Men between the ages of 50 and 75, healthy, with moderate benign prostatic hyperplasia, no signs of prostate cancer. A total of 240 men participated in the six-month trial.

Evaluation of the Experimental Results:

Effectiveness: 1. benign prostatic hyperplasia: IPSS, QOL, prostate volume, the maximal urinary flow rate, residual urine; 2. triglycerides; 3. lipoprotein cholesterol; 4. total bilirubin. Safety: occurrence, process, and solution of all adverse events during treatment.

Experimental Results:

I. Triglyceride and Lipoprotein Cholesterol Levels

1. Triglyceride:

After 24 weeks of administration, the levels of triglycerides in Group A (group of administration of 30 mg), Group B (group of administration of 90 mg), and Group D (group of administration of 60 mg) were decreased by 6.54%, 8.59%, and 8.58% on average, respectively, as compared with baseline. The results of statistical analysis showed that there was a statistically significant difference in the Group D before and after treatment (P<0.05). Correspondingly, in Group C (placebo group), there was only an average decrease of 2.33% (P>0.05). This result suggested that the test drug had the effect of lowering triglycerides. Preclinical animal experiment results also supported this conclusion.

TABLE 2

Changes in the mean value of triglyceride after 24 weeks administration as compared with baseline

|  | Group A (research drug 30 mg) | Group B (research drug 90 mg) | Group C (Placebo) | Group D (research drug 60 mg) |
|---|---|---|---|---|
| N(missing) | 50(10) | 48(12) | 50(10) | 56(4) |
| percentage of average change | −6.54% | −8.59% | −2.33% | −8.58% |
| P value | 0.114 | 0.477 | 0.228 | 0.016 |

Figure 2:
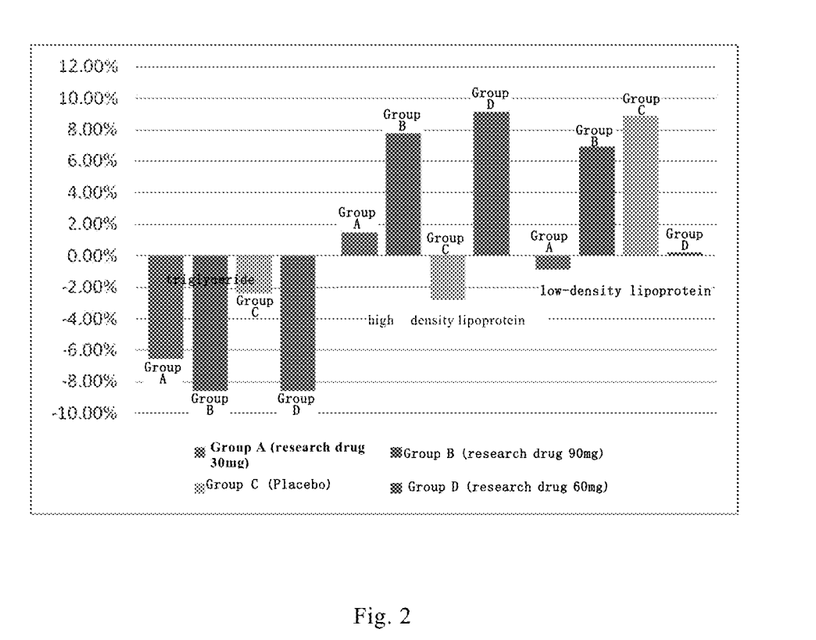
Figure 5:
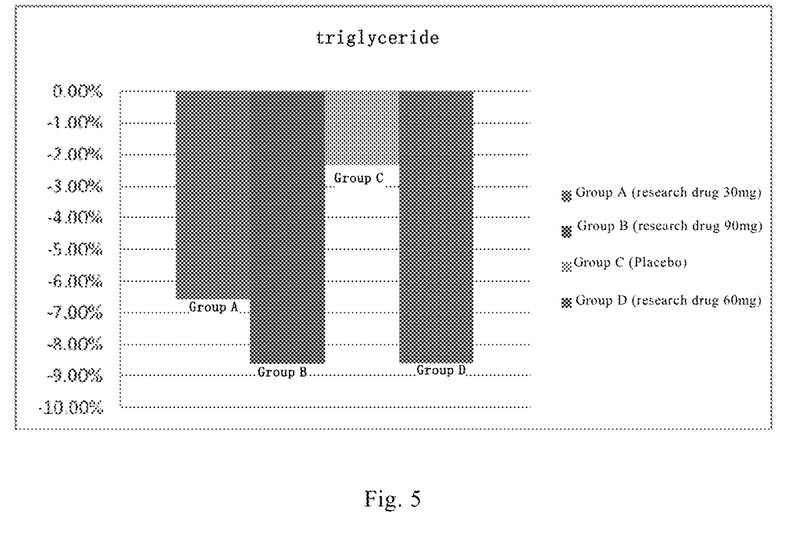
FIG. 5 shows changes of triglycerides from baseline in humans for 24 weeks. Compared with Group C (0 mg Group), triglycerides are decreased in Group A (30 mg Group), Group B (90 mg Group) and Group D (60 mg Group) before and after administration of triglyceride, wherein Groups B and D have a large extent.

The results are shown in Table 2 and FIGS. 2 and 5. As shown by the histogram, as compared with Group C, the triglyceride levels in Group A, Group B and Group D were significantly decreased after the administration, and the decrease in Group B and Group D was the most significant. Group D had a statistically significant difference (P<0.05).

The results indicated that the isothiocyanate compounds of the present invention (e.g., phenylethyl isothiocyanate) could significantly reduce the level of triglyceride in serum of the subject.

2 Lipoprotein Cholesterol

Among the 14 centers in the clinical trial, the serum triglyceride levels and high-density lipoprotein and low-density lipoprotein levels in serum of the subjects were all detected in the center No. 11, center No. 13, and center No. 14.

Results:

High-density lipoprotein: Compared with baseline, the serum high-density lipoprotein levels in the drug administration groups (Group A, Group B, and Group D) were significantly increased, and the order of the increase was shown as follows: Group A (group with the administration of 30 mg)<Group B (group with the administration of 90 mg)<D group (group with the administration of 60 mg); and in Group C (0 mg group), the serum high-density lipoprotein level was significantly decreased.

TABLE 3

Changes in serum high-density lipoprotein as compared with baseline after 24 weeks administration in Centers No. 11, 13 and 14

|  | Group A (30 mg) | Group B (90 mg) | Group C (Placebo) | Group D (60 mg) |
|---|---|---|---|---|
| N(missing) | 8(3) | 8(3) | 8(3) | 9(2) |
| average change value | 0.0063 | 0.0938 | −0.0356 | 0.1013 |
| percentage of average change | 1.45% | 7.77% | −2.76% | 9.15% |
| P value | 0.926 | 0.007 | 0.565 | 0.359 |

The results are shown in Table 3 and FIG. 2. As compared with baseline, high-density lipoprotein levels were increased in Group A (group with the administration of 30 mg), Group B (group with the administration of 90 mg), and Group D (group with the administration of 60 mg), wherein the increase in B group and D group was more significant. Group B (group with the administration of 90 mg) had a statistically significant difference (P<0.05) as compared to the placebo group (Group C), indicating that the isothiocyanate compounds of the present invention (e.g., phenylethyl isothiocyanate) could significantly increase the level of high density lipoprotein in serum of a subject.

Low-Density Lipoprotein:

TABLE 4

Changes in low-density lipoprotein as compared with baseline after 24 weeks of administration

|  | Group A (30 mg) | Group B (90 mg) | Group C (Placebo) | Group D (60 mg) |
|---|---|---|---|---|
| N(missing) | 8(3) | 8(3) | 8(3) | 9(2) |
| average change value | 0.0062 | 0.1925 | 0.2678 | −0.0425 |
| percentage of average change | −0.88% | 6.92% | 8.88% | 0.05% |
| P value | 0.971 | 0.429 | 0.098 | 0.818 |

The results are shown in Table 4 and FIG. 2. As compared with the increase of 8.88% in Group C, the low-density cholesterol levels of the drug administration groups (Group A, Group B, and Group D) were significantly decreased by −0.88%, 6.92% and 0.05%, respectively. Among them, the decrease in Group A was the most significant, indicating that the isothiocyanate compounds of the present invention (e.g., phenylethyl isothiocyanate) could significantly reduce the level of low density lipoprotein in serum of the subject.

Discussion:

After administration for 24 weeks, as compared with baseline, triglyceride levels in Group A (group with the administration of 30 mg), Group B (group with the administration of 90 mg), and Group D (group with the administration of 60 mg) were decreased by an average of 6.54%, 8.59% and 8.58%. The results of statistical analysis showed that there was a statistically significant difference in Group D before and after the treatment (P<0.05). There was only an average decrease of 2.33% (P>0.05) in Group C (placebo group). The decreasing trend of low-density lipoprotein was basically consistent with that of triglyceride. As compared with the Group C, the levels of high-density lipoprotein in the drug administration groups (Group A, Group B, and Group D) were significantly increased. These results indicated that the isothiocyanate compounds (such as phenylethyl isothiocyanate) of the present invention could not only lower the levels of triglyceride and low-density lipoprotein in serum of mammals, but also could increase high-density lipoprotein level in serum.

II. Total Bilirubin Levels

After 24 weeks of administration, the total bilirubin levels in Group A (group with the administration of 30 mg), Group B (group with the administration of 90 mg), and Group D (administered in the 60 mg group) were decreased by an average of 8.91%, 6.10%, and 8.55%, as compared with the baseline. The results of statistical analysis showed that there was a statistically significant difference in Group A, Group B and Group D before and after the treatment (P<0.05). However, there was only an average decrease of 1.57% in Group C (placebo group), with no statistical difference (P>0.05).

Figure 3:
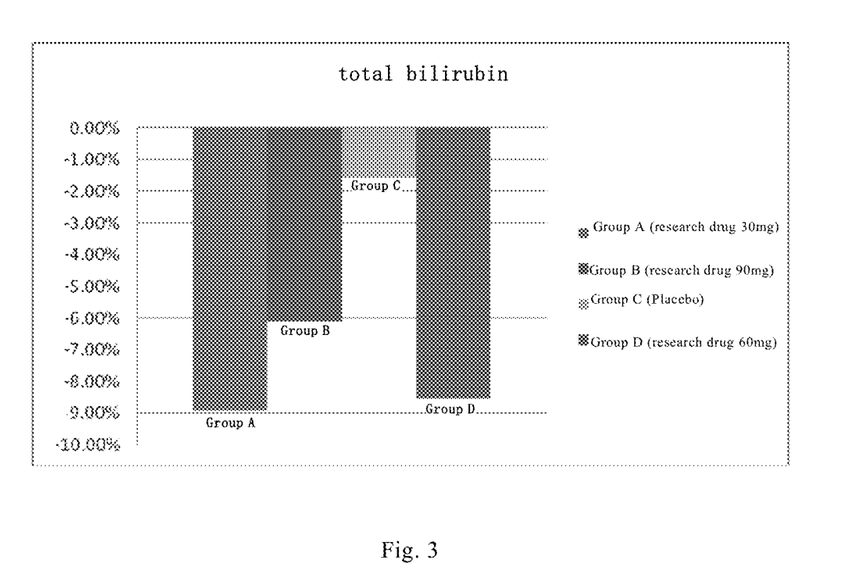
FIG. 3 shows that the levels of total bilirubin before and after administration in the administration group (Group A, Group B, and Group D) are decreased to some extent compared with Group C, and the decrease of total bilirubin before and after the administration in Group A and Group D is significantly different from that in Group C.
Figure 4:
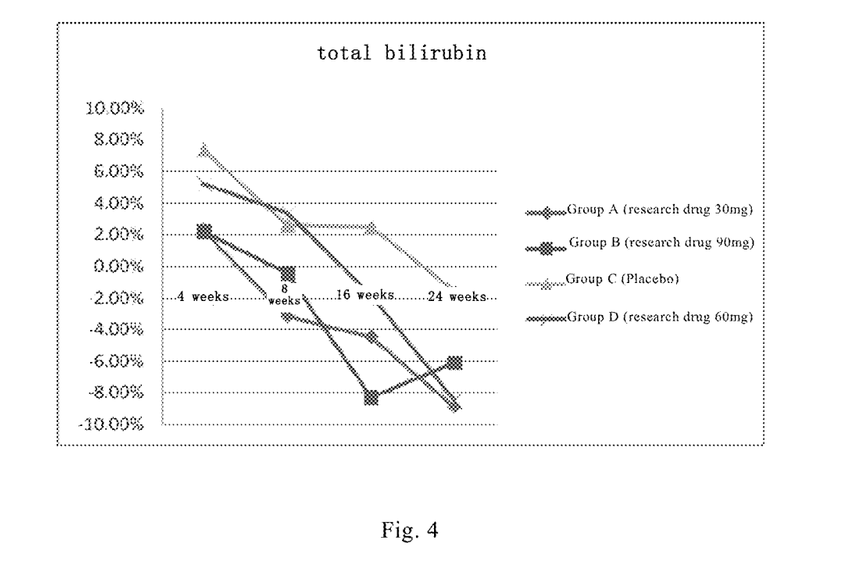
FIG. 4 shows the mean percentage change in total bilirubin from baseline 8 weeks prior to administration. Group A and Group B are essentially synchronized, and Groups C and D are essentially synchronized. After 8 weeks of administration, the total bilirubin levels of the administration groups (Group A, Group B, and Group D) are significantly decreased as compared with Group C.

The results are shown in Table 5, Table 6, FIG. 3 and FIG. 4. The results showed that, as compared with baseline, the total bilirubin levels in Group A (group with the administration of 30 mg), Group B (group with the administration of 90 mg), and Group D (group with the administration of 60 mg) were decreased significantly, and the P value in Group A was lower than 0.01, the P value in Group B was lower than 0.05, and the P value in Group D was lower than 0.001. The decrease of total bilirubin levels in any of the administration groups (Group A, Group D) was more significant than that in the placebo group (Group C).

TABLE 5

Changes of total bilirubin after 24 weeks of administration as compared with the baseline

|  | Group A (research drug 30 mg) | Group B (research drug 90 mg) | Group C (Placebo) | Group D (research drug 60 mg) |
| --- | --- | --- | --- | --- |
| N(missing) | 50(10) | 46(14) | 51(9) | 57(3) |
| percentage of average change | -8.91% | -6.10% | -1.57% | -8.55% |
| P value | 0.004 | 0.030 | 0.078 | <0.001 |

TABLE 6

Changes of total bilirubin after administration as compared with the baseline

|  |  | Group A (30 mg) | Group B (90 mg) | Group C (Placebo) | Group D (60 mg) |
| --- | --- | --- | --- | --- | --- |
|  | N(missing) | 50(10) | 46(14) | 51(9) | 57(3) |
| 4 weeks | percentage of average change | 2.23% | 2.18% | 7.38% | 5.21% |
|  | P value | 0.699 | 0.694 | 0.545 | 0.559 |
| 8 weeks | percentage of average change | -3.15% | -0.45% | 2.62% | 3.34% |
|  | P value | 0.136 | 0.188 | 0.568 | 0.539 |
| 16 weeks | percentage of average change | -4.46% | -8.28% | 2.49% | -1.82% |
|  | P value | 0.065 | 0.007 | 0.398 | 0.140 |
| 24 weeks | percentage of average change | -8.91% | -6.10% | -1.57% | -8.55% |
|  | P value | 0.004 | 0.030 | 0.078 | <0.001 |

As shown in Table 5, Table 6, and FIG. 3, the levels of total bilirubin before and after the administration in Group A, Group B, and Group D were decreased to some extent as compared with Group C, and the decrease of total bilirubin before and after the administration in Group A or Group D was significantly different from that in Group C. The P value in Group A was lower than 0.01, the P value in Group B was lower than 0.05, and the P value in Group D was lower than 0.001.

As shown in FIG. 4, the percentage of average change of total bilirubin as compared with the baseline before 8 weeks of the administration was shown as follows: Group A and Group B were basically synchronized, and Groups C and D were basically synchronized. After 8 weeks of administration, total bilirubin levels were significantly decreased in Group A, Group B, and Group D as compared with Group C.

Discussion:

The results of the 4, 8, 16 and 24 weeks of administration showed that the decrease in the total bilirubin level of the subjects was gradually significant with the increase of time of administration. The P value of the statistical analysis results reflected this trend in a digital manner.

After 24 weeks of administration, the total bilirubin levels in Group A (group with the administration of 30 mg), Group B (group with the administration of 90 mg), and Group D (group with the administration of 60 mg) were decreased by an average of 8.91%, 6.10%, and 8.55%, respectively, as compared with the baseline.

After 24 weeks of the administration, there was a statistically significant difference in Group A, Group B and Group D (P<0.05), while Group C (placebo group) was not statistically significant (P>0.05).

The above results indicated that isothiocyanate compounds such as phenylethyl isothiocyanate could also significantly reduce the level of total bilirubin in human serum.

In summary, in both an SD rat animal experiment and a clinical human experiment, the results showed that the isothiocyanate compounds of the present invention (such as phenylethyl isothiocyanate) could significantly reduce triglyceride level in serum. Moreover, the clinical human experiment results showed that isothiocyanate compounds (such as phenylethyl isothiocyanate) could also lower the level of low-density lipoprotein in serum, while significantly increase the level of high-density lipoprotein.

The currently used hypolipidemic medicines in the clinic are usually synthetic compounds that are effective on a single target and obtained by high-throughput screening focusing on a single target based a library containing thousands of compounds. However, current research is usually limited by the understanding of the role of a single target. The effects of a compound on other genes, as well as the regulation and feedback in the body caused by the effects of the medicine on the single target are usually unclear. Hyperlipidemia is a chronic condition which means a long-term use, and the above unclear effects may cause a negative impact on other aspects of the subject.

However, the isothiocyanate compounds studied in the present invention are derived from nature. For example, phenylethyl isothiocyanate is derived from Brassicaceae vegetables such as vegetables, radishes, and Chinese cabbage and the like, and therefore it is safe. Since it is derived from nature and is not obtained via a single target screening, the compound of the present invention can simultaneously reduce low density lipoprotein, and triglyceride, and increase high-density lipoprotein.

Summing up, the above results have indicated that the isothiocyanate compounds of the present invention (such as phenylethyl isothiocyanate) can significantly reduce total bilirubin levels, triglycerides and low density lipoprotein levels in serum, and can significantly increase high-density lipoprotein levels.

Moreover, such compounds can not only prevent and/or treat hyperbilirubinemia, but also can reduce triglyceride and low-density lipoprotein, increase high density lipoprotein, and prevent and/or treat high triglyceride, high lipoprotein cholesterol.

Example 3 Auxiliary Detection on Total Bilirubin and Blood Lipid

Using the same method as described in Example 2, 24 volunteers with benign prostatic hyperplasia accompanied by elevated bilirubin were recruited. Using the same manner as described in Example 2, subjects meeting the entry criteria were randomly assigned into any of the following four groups at a ratio of 1:1:1:1: administration group (Group A): phenylethyl isothiocyanate 10 mg/time, 3 times a day; administration group (Group D): Phenylethyl isothiocyanate 20 mg/time, 3 times a day; administration group (Group B): phenylethyl isothiocyanate 30 mg/time, 3 times a day; placebo group (C group): phenylethyl isothiocyanate placebo 1 capsule/time, 3 times a day. Oral administration was continued for 24 weeks.

The effectiveness and safety of the experiment were evaluated. Effectiveness: 1. benign prostatic hyperplasia: IPSS, QOL, prostate volume, maximal urinary flow rate, residual urine; 2. triglycerides; 3. lipoprotein cholesterol; 4. total bilirubin. Safety: occurrence, process, and solution of all adverse events during treatment.

The results showed that after the isothiocyanate compounds (such as phenylethyl isothiocyanate) of the present invention were taken by the volunteers, the total bilirubin level, triglyceride and low density lipoprotein levels were significantly decreased by 15-25%, and the high-density lipoprotein level was increased significantly by 10-20%.

Example 4 Auxiliary Detection on Blood Lipids

Using the same method as described in Example 3 except that 8 volunteers with only hyperlipidemia were recruited and using the same method as described in Example 3. The volunteers were randomly assigned into the following four groups at a ratio of 1:1:1:1: administration group (Group A): phenylethyl isothiocyanate 10 mg/time, 3 times a day; administration group (Group D): phenylethyl isothiocyanate 20 mg/time, 3 times a day; administration group (Group B): phenylethyl isothiocyanate 30 mg/time, 3 times a day; placebo group (Group C): phenylethyl isothiocyanate placebo 1 capsule/time, 3 times a day. Oral administration was continued for 6 weeks.

The results showed that after the isothiocyanate compounds (such as phenylethyl isothiocyanate) of the present invention were taken by the volunteers, the levels of triglyceride and low density lipoprotein were significantly decreased, wherein the triglyceride and low density lipoprotein levels were decreased by 10-25%, and high-density lipoprotein levels was increased significantly by 10-20%.

Example 5 Auxiliary Detection on Total Bilirubin

The method was the same as described in Example 3, except that 8 volunteers with only hyperbilirubinemia were recruited in the medical research peers.

Using the same manner as described in Example 3, the subjects were randomly assigned into any one of the following four groups at a ratio of 1:1:1:1: administration group (Group A): phenylethyl isothiocyanate 10 mg/time, 3 times a day; administration group (Group D): phenylethyl isothiocyanate 20 mg/time, 3 times a day; administration group (Group B): phenylethyl isothiocyanate 30 mg/time, 3 times a day; placebo group (C group): phenylethyl isothiocyanate placebo 1 capsule/time, 3 times a day. Oral administration was continued for 6 weeks.

The results showed that the total bilirubin level was significantly decreased after the isothiocyanate compounds of the present invention (such as phenylethyl isothiocyanate) were taken by the volunteers, and the decrease was 10-25%.

The invention claimed is:

1. A method of preventing and/or treating hyperbilirubinemia, comprising administering a compound to a mammal in need thereof,
   wherein the compound is phenylethyl isothiocyanate, the hyperbilirubinemia is selected from the group consisting of: hemolytic jaundice, hepatic jaundice, cholestasis, gilbert syndrome, and a combination thereof.

2. The method of claim 1, wherein the mammal is a human.

3. The method of claim 1, wherein an administration dose is 0.01-100 mg/kg/day.

4. The method of claim 1, wherein an administration frequency is 1-5 times/day.

5. The method of claim 1, wherein the administering is conducted one or more cycles, and each cycle is 2-60 days.

6. The method of claim 3, wherein an administration dose is 0.1-50 mg/kg/day.

7. The method of claim 6, wherein an administration dose is 0.5-20 mg/kg/day.

8. The method of claim 4, wherein an administration frequency is 1-3 times/day.

9. The method of claim 5, wherein each cycle is 7-30 days.

* * * * *